(12) United States Patent
Kraus et al.

(10) Patent No.: US 11,759,140 B2
(45) Date of Patent: Sep. 19, 2023

(54) METHODS AND SYSTEMS TO DETERMINE THE NEURAL REPRESENTATION OF DIGITALLY PROCESSED SOUNDS

(71) Applicant: Northwestern University, Evanston, IL (US)

(72) Inventors: Nina Kraus, Evanston, IL (US); Trent George Nicol, Evanston, IL (US); Jennifer Lynn Krizman, Evanston, IL (US); Travis White-Schwoch, Evanston, IL (US)

(73) Assignee: Northwestern University, Evanston, IL (US)

( * ) Notice: Subject to any disclaimer, the term of this patent is extended or adjusted under 35 U.S.C. 154(b) by 515 days.

(21) Appl. No.: 16/649,899

(22) PCT Filed: Sep. 26, 2018

(86) PCT No.: PCT/US2018/052870
§ 371 (c)(1),
(2) Date: Mar. 23, 2020

(87) PCT Pub. No.: WO2019/067551
PCT Pub. Date: Apr. 4, 2019

(65) Prior Publication Data
US 2020/0305755 A1 Oct. 1, 2020

Related U.S. Application Data

(60) Provisional application No. 62/563,999, filed on Sep. 27, 2017.

(51) Int. Cl.
A61B 5/38 (2021.01)
A61B 5/12 (2006.01)
A61B 5/378 (2021.01)

(52) U.S. Cl.
CPC ............ *A61B 5/38* (2021.01); *A61B 5/121* (2013.01); *A61B 5/378* (2021.01)

(58) Field of Classification Search
CPC .......... A61B 5/38; A61B 5/121; A61B 5/378; A61B 5/00
See application file for complete search history.

(56) References Cited

U.S. PATENT DOCUMENTS 10,736,535 B2 * 8/2020 Elberling .............. A61B 5/6815
10,825,353 B2 * 11/2020 Roberts ................. G10L 21/003
(Continued)

OTHER PUBLICATIONS

Anderson, S., et al. (2013). The potential role of the cABR in assessment and management of hearing impairment. Int J Otolaryngol, 2013, 604729.
(Continued)

*Primary Examiner* — Oyesola C Ojo
(74) *Attorney, Agent, or Firm* — Quarles & Brady LLP

(57) ABSTRACT

The present disclosure relates to methods for evaluating the sound quality of a digital engineering process by, in part, measuring the frequency following response (FFR) of the human auditory system elicited by identical auditory stimuli (e.g., a musical interval) encoded with variations of a digital signal processing technique (e.g., various sampling rates). Once measured, the FFR may be analyzed to determine the comparative effect of each digital signal processing technique on a human subject's ability to process complex stimuli presented by the digital engineering process.

17 Claims, 7 Drawing Sheets

(56) References Cited

U.S. PATENT DOCUMENTS

| | | | | |
|---|---|---|---|---|
| 10,921,888 | B2* | 2/2021 | Schiff | A61B 5/38 |
| 2012/0197153 | A1* | 8/2012 | Kraus | A61B 5/38 |
| | | | | 600/545 |
| 2013/0101128 | A1* | 4/2013 | Lunner | A61B 5/6815 |
| | | | | 381/60 |
| 2013/0208934 | A1* | 8/2013 | Chaiupper | H04R 25/70 |
| | | | | 381/321 |
| 2015/0005660 | A1* | 1/2015 | Kraus | A61B 5/375 |
| | | | | 600/545 |
| 2015/0350794 | A1* | 12/2015 | Pontoppidan | A61B 5/125 |
| | | | | 381/321 |
| 2016/0217267 | A1* | 7/2016 | Kraus | A61B 5/38 |
| 2016/0235328 | A1* | 8/2016 | Elberling | A61B 5/38 |

OTHER PUBLICATIONS

Chandrasekaran, B., et al. (2010). The scalp-recorded brainstem response to speech: origins and plasticity. Psychophysiology, 47 (2010), 236-246.

Gorga, M., Abbas, P., & Worthington, D. (1985) Stimulus calibration in ABR measurements. In J. Jacobson (Ed.), The auditory brainstem response (pp. 49-62). SanDiego, CA: College-Hill Press.

He, S., et al. (2012). Auditory Discrimination: The Relationship Between Psychophysical and Electrophysiological Measures. International Journal of Audiology, 51(10), 771-82.

Killion, M. (2009). What Special Hearing Aid Properties Do Performing Musicians Require? The Hearing Review, Feb. 2009, 20-31.

Kim, J. (2015) Acoustic Change Complex: Clinical Implications Journal of Otology and Audiology, 19(3), 120-124.

Kraus, N. & White-Schwoch, T. (2015). Unraveling the biology of auditory learning: A cognitive-sensorimotor-reward framework. Trends in Cognitive Sciences, 19(11), 642-654.

Kraus, N. (2011). Listening in on the listening brain. Physics Today, 64(6), 40-45.

Lee, K.M., et al. (2015). Neural transformation of dissonant intervals in the auditory brainstem. Music Perception, 32 (5), 445-459.

Liu, L., et al. (2005). Phase-locked responses to pure tones in the inferior colliculus. Journal of Neurophysiology, 95 (3), 1926-1935.

Martin, G.K., Probst, R., & Lonsbury-Martin, B. L. (1990). Otoacoustic emissions in human ears: Normative findings. Ear and Hearing, 11, 106-120.

Meyer, B., & Moran, D. (2007). Audibility of a CD-Standard A/DA/A Loop Inserted into High-Resolution Audio Playback. Journal of the Audio Engineering Society, 55(9), 775-779.

Moore, B. C. J., et al. (2003). Perceived naturalness of spectrally distorted speech and music. The Journal of the Acoustical Society of America, 114(1), 408.

Nyquist, H. (2002). Certain Topics in Telegraph Transmission Theory. Proceedings of the IEEE, 90(2). (Reprinted from Transactions of the A. I. E. E., pp. 617-644, Feb. 1928).

Oohashi, T., et al. (2000). Inaudible high-frequency sounds affect brain activity: Hypersonic effect. Journal of Neurophysiology, 83(6), 3548-3558.

Pras, A., et al. (2009). Subjective Evaluation of MP3 Compression for Difference Musical Genres. Paper presented at the 127th Audio Engineering Society Convention, New York, Oct. 9-12.

Pras, A., et al. (2010). Sampling rate discrimination: 44.1 kHz vs. 88.2 kHz. Paper presented at the 128th Audio Engineering Society Convention, London, May 22-25.

Robles, L., et al. (1991). Two-tone distortion in the basilar membrane of the cochlea. Nature, 349, 413-414.

Schweitzer, C. (1997). Development of Digital Hearing Aids. Trends in Amplification, 2(2), 41-77.

Shannon, C. E. (1949). Communication in the presence of noise. Proceedings of the IRE, 37(1), 10-21.

Skoe, E., et al. (2010). Auditory brain stem response to complex sounds: A tutorial. Ear and Hearing, 31, 302-324.

Sohmer, H., et al. "Cochlear, brain stem, and cortical evoked responses in nonorganic hearing loss." Annals of Otology, Rhinology & Laryngology 86.2 (1977): 227-234.

White-Schwoch, T., et al. (2016). Individual Differences in Human Auditory Processing: Insights From Single-Trial Auditory Midbrain Activity in an Animal Model. Cereb Cortex, 2016, 1-21.

Wiley, T. L., et al. (1996). Tympanometric measures in older adults. Journal of the American Academy of Audiology, 7, 260-268.

Allen, J., et al. (2000). Neural representation of consciously imperceptible speech sound differences. Perception and Psychophysics, 62(7), 1383-1393.

Aiken, S. J., et al. "Envelope and spectral frequency-following responses to vowel sounds." Hearing research 245.1-2 (2008): 35-47.

International Searching Authority, International Search Report and Written Opinion for application PCT/US2018/052870 dated Dec. 13, 2018.

* cited by examiner

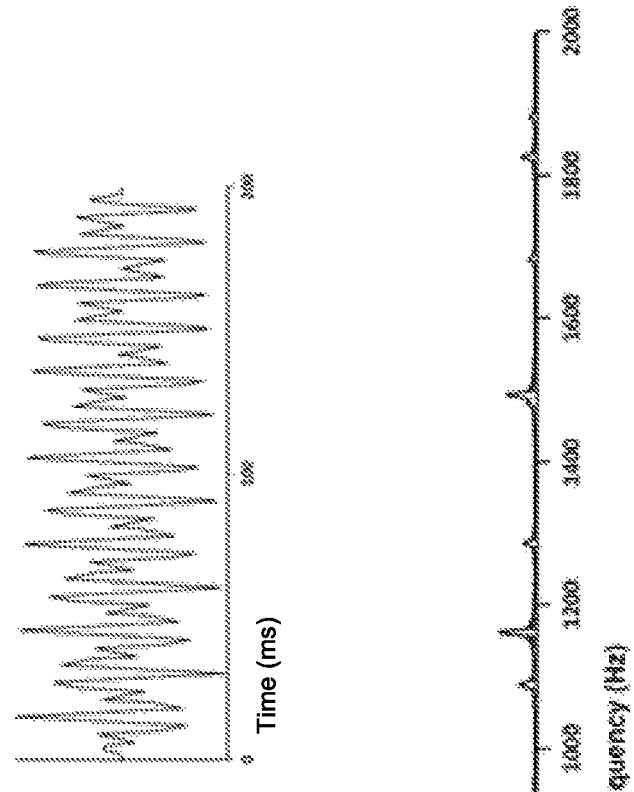
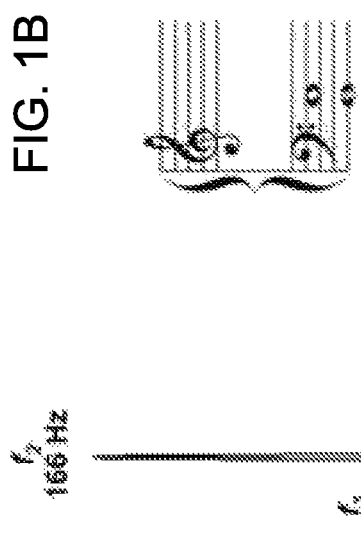
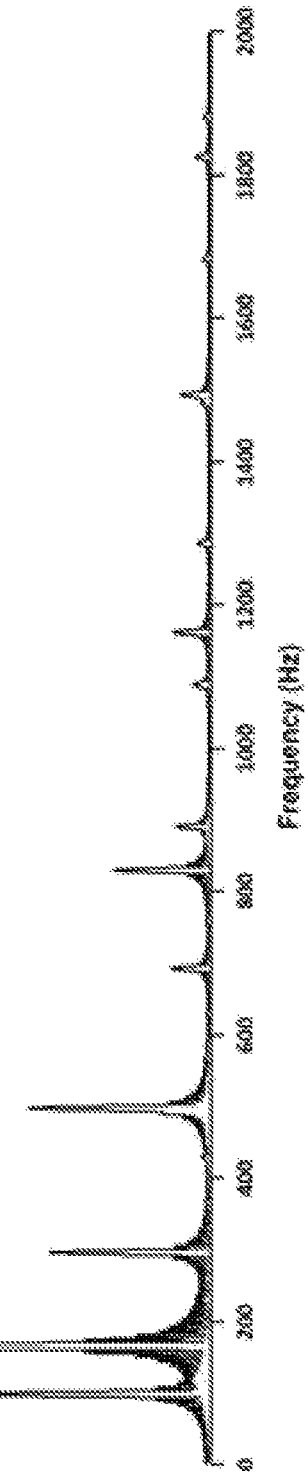
FIG. 1C
FIG. 1B
FIG. 1A

METHODS AND SYSTEMS TO DETERMINE THE NEURAL REPRESENTATION OF DIGITALLY PROCESSED SOUNDS

CROSS REFERENCE TO RELATED APPLICATIONS

The present application is the U.S. national stage entry of international application PCT/US2018/052870, filed Sep. 26, 2018, which claims the benefit of U.S. Provisional Application 62/563,999, filed Sep. 27, 2017, the contents of which are incorporated herein by reference in their entireties.

TECHNICAL FIELD

Aspects of the present disclosure relate to digitally processed sound.

BACKGROUND

Audio engineering and audio device development generally involve the development of digital signal processing algorithms to generate, manipulate, and sonify signals for devices including headphones, speakers, hearing aids, and the like. Conventional methods for evaluating the efficacy of such digital signal processing techniques rely on subjective ratings offered by one or more "golden eared", human listeners. More specifically, in response to hearing multiple versions of a sound, a "golden eared" listener provides a subjective rating of the quality of the sound. Evaluating sounds in such a manner is time consuming, labor-intensive, and error prone.

Accordingly, improved and objective evaluation methods are needed.

BRIEF DESCRIPTION OF THE DRAWINGS

The accompanying figures, which are incorporated herein and constitute part of this specification, illustrate non-limiting and non-exhaustive embodiments of the present disclosure, and, together with the description provided herein, serve to explain various features of the invention.

FIG. 1A depicts the spectrum of an auditory stimulus presented at a sampling rate of 96 kHz, as described in the Examples herein. The two fundamental frequencies, 99 Hz ($f_1$) and 166 Hz ($f_2$), were created with equal intensity. The observed difference in intensity is attributed to inherent characteristics of the presentation system. FIG. 1B illustrates a Major $6^{th}$ chord, G2 and E3. The depicted musical interval used in the Examples comprises the fundamental frequencies 99 and 166 Hz, corresponding to a Major $6^{th}$ chord, G2 and E3, respectively. FIG. 1C depicts a MATLAB-generated time domain waveform of the musical interval used in the Examples.

SUMMARY

Figure 2:
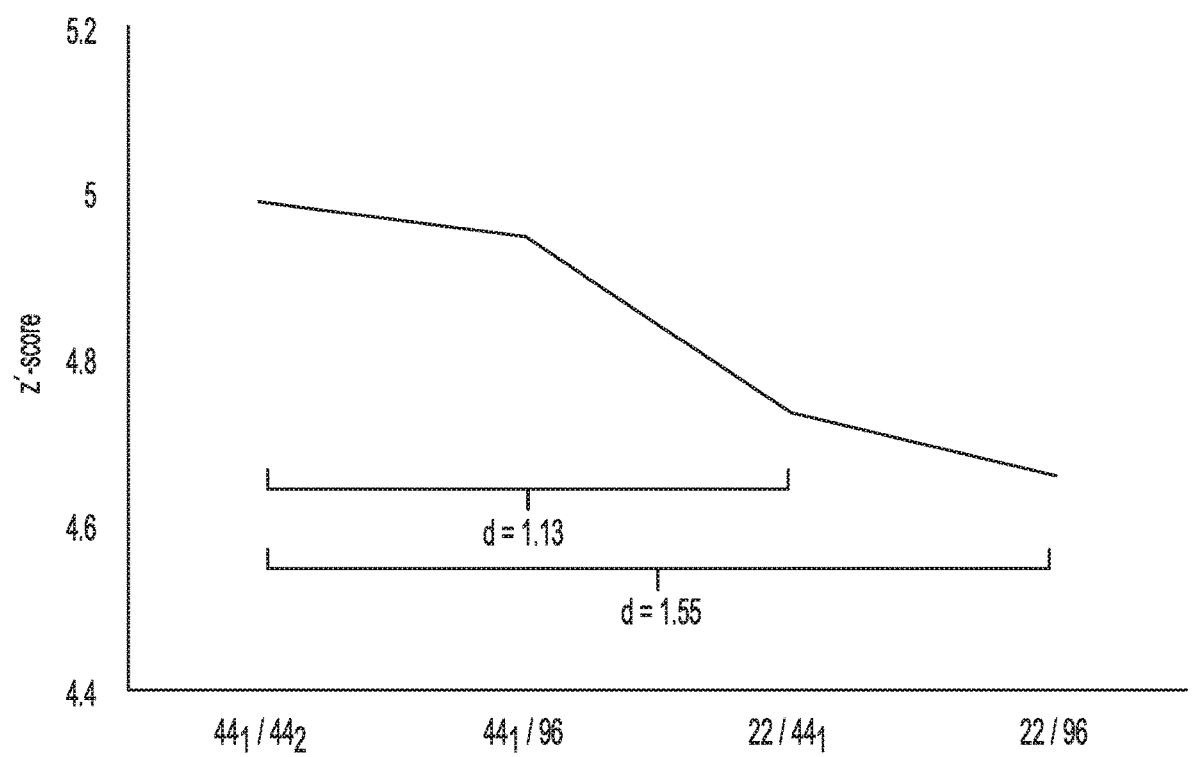
FIG. 2 depicts a graph of a stimulus correlation analysis, including three test comparisons ($22/44_1$; $22/96$; $44_1/96$) and a control comparison ($44_1/44_2$), as described in the Examples herein. Although all comparisons show very high correlation, a decrease is noted for the two comparisons involving the 22 kHz stimulus. Cohen's effect size calculations confirmed that there was a meaningful difference between the strength of the control-condition inter-stimulus correlations and the two conditions involving the 22 kHz correlations: $44_1/44_2$ vs. $44_1/22$ (d=1.13); and $44_1/44_2$ vs. $96/22$ (d=1.55). The $44_1/96$ comparison did not meaningfully differ from the control (d=0.06).

Aspects of the present disclosure involve various systems and methods for determining how the brain distinguishes between variations of a digital sound, thereby indicating whether and to what extent digital processing impacts how the human brain processes sounds. More specifically and in one non-limiting example, the disclosed system includes the application of a series of algorithms to determine the extent to which the human brain distinguishes between sounds presented at three different sampling rates. A Frequency Following Response (FFR) of the human auditory brainstem may be used to record and analyze neural activity in response to auditory stimuli, such as digital signals. Measurable changes in the FFR are a more sensitive and reliable measure of the effect of digital engineering processes on the experience of a listener, as compared to conventional perceptual measurements of the human auditory system.

While the examples discussed herein relate to determining the extent to which the human brain distinguishes between a sound presented at various sampling rates, it is contemplated that any number of other digital signal processes could be applied, including filters, noise cancellation algorithms, pitch altering algorithms, distortions, amplifications, and more. Additionally, the present disclosure could apply to comparisons of multiple pieces of hardware, such as two or more pairs of headphones or two or more hearing aids.

In one aspect, the disclosed technology relates to a method for developing an audio device, the method including: (a) presenting at least two auditory stimuli to a subject, wherein each auditory stimulus is created by a process that uses different variations of the same digital signal processing technique; (b) measuring the frequency following response (FFR) elicited by each stimulus and comparing the measurements to identify any positive or negative effects in the FFR elicited by any one of the stimuli; and (c) developing an audio device that converts an analog auditory signal into a digital auditory signal using the digital processing technique determined in step (b) to have a more positive effect or less negative effect on FFR. In one embodiment, an audio device is produced by the method. In another embodiment, the audio device is an assistive listening device, a speaker, an earphone, or headphones. In another embodiment, the assistive listening device includes a hearing aid or cochlear implant. In another embodiment, the digital signal processing technique is a filter, a noise cancellation algorithm, a noise reduction algorithm, a pitch-altering algorithm, a compression algorithm, a distortion, an amplification, or a variation in sampling rate, bit depth, or bit rate. In another embodiment, measuring the FFR includes measuring harmonics and/or distortion products generated by the auditory system that are not present in the stimuli. In another embodiment, measurements of harmonics and/or distortion products present in the FFR but not present in the stimuli are compared to identify any positive or negative effects in the FFR elicited by any one of the stimuli. In another embodiment, the at least two auditory stimuli are generated from the same source.

In another aspect, the disclosed technology relates to a method for evaluating the sound quality of a digital engineering process, including: (a) presenting a first auditory stimulus to a subject, wherein the first auditory stimulus is created by a digital engineering process that uses a first digital signal processing technique; (b) presenting a second auditory stimulus to a subject, wherein the second auditory stimulus is created by the digital engineering process of step (a) but using a variation of the first digital signal processing technique; (c) measuring the frequency following response (FFR) elicited by each of the first and second auditory stimuli, and comparing the measurements to determine the effect of each stimulus on FFR; and (d) identifying the digital engineering process of step (a) or step (b) resulting in the more positive effect or less negative effect on FFR as the process that provides superior sound quality. In one embodiment, the digital signal processing technique is a filter, a noise cancellation algorithm, a noise reduction algorithm, a pitch-altering algorithm, a compression algorithm, a distortion, an amplification, a variation in sampling rate, bit depth, or bit rate. In another embodiment, the digital signal processing technique is a sampling rate. In another embodiment, the sampling rate is in the range of 22 kHz to about 44 kHz. In another embodiment, the variation of the first digital signal processing technique is the absence of the first digital signal processing technique. In another embodiment, the first and second auditory stimuli are generated from the same source.

In another aspect, the disclosed technology relates to an assistive listening device, including a digital engineering process that includes a sampling rate of at least 22 kHz. In one embodiment, the sampling rate is not greater than about 44 kHz. In another embodiment, the device includes a hearing aid or cochlear implant.

In another aspect, the disclosed technology relates to a system for evaluating the sound quality of a digital engineering process, the system including a computing device including at least one processor configured to perform a method for evaluating the sound quality of a digital engineering process. In one embodiment, the digital signal processing technique is a filter, a noise cancellation algorithm, a noise reduction algorithm, a pitch-altering algorithm, a compression algorithm, a distortion, an amplification, a sampling rate, a bit depth, or a bit rate. In another embodiment, the at least one processor is further configured to measure harmonics and/or distortion products generated by the auditory system that are not present in the stimuli.

DETAILED DESCRIPTION

Analog-to-digital (AD) conversion of audio signals has become a fundamental component of how listeners experience sound in the modern world. An increasingly large percentage of auditory signals, including speech and music, are now experienced as electro-acoustically regenerated, discrete-time digital representations of original continuous-time analog signals. Consideration for each step in the analog-to-digital transformation and the effect on listener perception and physiology is imperative for researchers and clinicians working in the audio realm of the twenty-first century.

A fundamental component of AD conversion is sampling rate. The digitization of an analog signal requires that discrete time points be selected from a continuous waveform, a process known as sampling. The number of times per second that an analog signal is sampled is the sampling rate, expressed in kHz. Faithful reproduction is governed by the sampling theorem, or Nyquist-Shannon theorem, which states that all information within a continuous-time signal with a finite bandwidth and no frequency higher than W Hz can be faithfully represented as a discrete sequence of samples, provided that the samples are spaced ½ W seconds apart. This discovery provided the theoretical basis for a universally accepted rule in the digitization of audio: to maintain full fidelity, an analog signal must be sampled at a rate that is at least twice the highest frequency component contained within the signal. The impact of this theorem is reflected in the current sampling rate standards for the production of electronic devices across multiple industries, including manufacturers of music equipment and assistive devices (e.g. hearing aids).

Commonly used sampling rates for the recording and transmission of audio include 8 kHz (telephone), 22.05 kHz (AM radio), 32 kHz (FM radio), 44.1 kHz (compact-disc), 48 kHz (DVD audio), and 96-192 kHz (high-fidelity music). Digital hearing aids were developed using sampling rates ranging between 16 and 32 kHz, depending on both manufacturer and model. Review of literature provided by several current hearing aid manufacturers (Starkey, Oticon, Widex, Phonak) revealed that these rates have remained stable in the current hearing aid market, typically attributed to restrictions imposed by power supply, device size, and transducer limitations. The present disclosure focuses on sampling rates used in the digitization of audio frequencies, not the much higher frequencies that are used as carriers in the transmission of audio signals, such as the 2.4 GHz ISM band used in wireless transmission.

Considering the range of human hearing (up to about 20 kHz), 44.1 kHz is the most commonly used sampling rate that is high enough to encode all audible content of an analog signal. However, non-biological factors have influenced the selection of sampling rates, including compatibility with other technology (e.g. DVD audio), efficient transmission of data (e.g. telephone, radio), power supply and size restrictions (e.g. hearing aids), and the desire for extremely high-fidelity sound in the entertainment industry.

The present disclosure provides methods to validate the effect of various digital signal processing techniques on the conversion of an analog auditory signal into a digital auditory signal. As used herein, the conversion of an analog auditory signal into a digital auditory signal is referred to as "a digital engineering process." The effect of a digital engineering process on the experience of a listener can be much more reliably and sensitively measured based on quantifiable changes in FFR, as described herein, as compared to previously used subjective measurements of perception.

In the context of the present disclosure, the concept of evaluating the effect of a digital signal processing technique refers to determining whether the use of a first digital signal processing technique in a digital engineering process results in either a measurable positive effect or no measurable negative effect in the FFR of a listener as compared to a digital engineering process that lacks the technique. If so, the digital engineering process that includes the first digital signal processing technique provides sound quality superior to that of the compared digital engineering process. This concept also includes determining whether a certain first variation of a first digital signal processing technique results in either a measurable positive effect or no measurable negative effect in the FFR of a listener as compared to a digital engineering process that uses a second different variation of the technique. If so, the digital engineering process that includes the first variation of the digital signal processing technique provides sound quality superior to that of the compared digital engineering process. Non-limiting examples of digital signal processing techniques include use of a filter, a noise cancellation algorithm, a noise reduction algorithm, a pitch-altering algorithm, a compression algorithm, a distortion, an amplification, and variations in the sampling rate, bit depth, or bit rate.

In embodiments where the digital signal processing technique is the use of digital sampling, the variations in the technique may be variations in the sampling rate. In various embodiments, the sampling rate may be at least about 22 kHz—for example, about 22 kHz, about 23 kHz, about 24 kHz, etc. In further embodiments, the sampling rate may be at least about 25 kHz, at least about 30 kHz, at least about 35 kHz, or at least about 40 kHz. In still further embodiments, the sampling rate may be about 35 kHz, about 36 kHz, about 37 kHz, about 38 kHz, about 39 kHz, about 40 kHz, about 41 kHz, about 42 kHz, about 43 kHz, or about 44 kHz.

Measuring the FFR is a non-invasive method of recording neural activity in response to auditory stimuli—e.g., an acoustic sound, such as a complex sound. Non-limiting examples of suitable auditory stimuli include natural, synthetic, and hybrid complex sounds, such as musical intervals, musical sounds, vocal sounds, environmental sounds, and combinations thereof. In some embodiments, the auditory stimuli are generated from the same source. In one such instance, an initial acoustic sound may be generated and then processed by a single hardware device using variations of a certain digital processing signal technique. In another such instance, an initial acoustic sound may be generated and then processed by different hardware devices using variations of a certain digital processing signal technique.

While the FFR is primarily a subcortically-generated potential (Chandrasekaran & Kraus, 2010), its activity represents a confluence of cognitive, sensorimotor, and reward networks (Kraus & White-Schwoch, 2015). Evoked potentials elicited by numerous repetitions of an auditory stimulus are recorded using contact electrodes on the scalp. Responses are then averaged to minimize variable background neural activity and isolate the relevant, invariant sound-evoked response. The FFR mirrors the spectral and temporal characteristics of the evoking stimulus with remarkable fidelity within the limits of the response bandwidth (Kraus, 2011). Moreover, this measure captures the nonlinear aspects of auditory processing, including harmonics and distortion products generated by the auditory system that are not present in the evoking stimulus.

FFR may be measured by presenting an acoustic stimulus comprising a complex sound to a subject and recording the brain's response to the acoustic stimulus. Brain response can be recorded in a number of different ways. For example, the brain's response can be measured using electrodes that pick up electrical potentials generated by populations of neurons in the brain of the subject—i.e., the electrodes measure voltage potentials evoked by the acoustic stimulus presented to the subject. The FFR measurement reflects sustained neural activity over a population of neural elements.

EXAMPLES

The following example is included to demonstrate various embodiments of the present disclosure. The use of this and other examples anywhere in the specification is illustrative only, and in no way limits the scope and meaning of the invention or of any exemplified form. Likewise, the invention is not limited to any particular preferred embodiments described herein. Indeed, modifications and variations of the invention may be apparent to those skilled in the art upon reading this specification, and can be made without departing from its spirit and scope. The invention is therefore to be limited only by the terms of the claims, along with the full scope of equivalents to which the claims are entitled.

Example 1

This example describes a study in which subjects were presented with acoustic signals comprising a complex sound—namely, a musical interval. The digital signal processing technique in this example is the use of differing sampling rates, and measurements of FFR were used to validate that different sampling rates have a significant effect on the neural representation of a musical interval. The use of the foregoing acoustic stimulus is representative of acoustic stimuli that are suitable for use in connection with the present disclosure. Hence, other natural, synthetic, and/or a hybrid complex sounds may also be used. Likewise, the use of the foregoing digital processing techniques and measurements of FFR are also representative of other digital processing techniques and measurements of FFR that are suitable for use in connection with the present disclosure. See, for example, U.S. Patent Publication No. 2016/0217267, hereby incorporated by reference in its entirety.

Experimental Method: Subjects. Twelve young adults (6 male, 6 female; age range 18-28) were recruited for participation in the study by word-of-mouth from the Evanston campus of Northwestern University. All subjects were monolingual English-speakers, had no history of otologic or neurologic dysfunction (self-report), and showed normal click-evoked ABR latencies (Bio-logic Navigator Pro; Natus Medical Incorporated). Subjects were evaluated for normal peripheral auditory function on the day of testing through distortion-product otoacoustic emission (DPOAE) testing (Bio-logic Scout; Natus Medical Incorporated) and 226 Hz tympanometry (easyTymp; MAICO Diagnostics) in each ear. All subjects exhibited middle ear pressure and immittance within normal limits (Wiley, 1996) and exhibited present DPOAEs from 1 to 8 kHz, measured using accepted methodology and in reference to normative data (Martin et al., 1990).

Experimental Method: Stimulus Creation. Three stimulus conditions were used in FFR measurement. The three stimuli differed only in sampling rate, including 22.05, 44.10, and 96.00 kHz, hereafter referred to as "22," "44," and "96," respectively. These sampling rates were chosen to 1) include values representative of the range of sampling rates in modern media recording and reproduction devices, and 2) include a rate that falls within the range used in assistive devices, i.e., 22.05 kHz. All stimuli were digitally created triangle-wave intervals (MATLAB R2013a; The MathWorks, Inc.) consisting of equal-amplitude fundamental frequencies 99 and 166 Hz, corresponding to the musical interval of a major sixth (E2 and G2) (FIG. 1). This frequency interval may be employed with the use of a digital synthesizer. Expected response frequencies were established relative to fundamental frequencies (Lee et al., 2015). Each stimulus was 200 ms in length, with a 10 ms Hanning-function attack and release.

Experimental Method: Stimulus Presentation. Stimuli were presented diotically (identical, simultaneous presentation to both ears) through ER2 insert earphones (Etymotic Research) at an intensity of 70.5±0.2 dB sound pressure level (SPL) with an inter-stimulus interval of 85 ms (AUDCPT, Neuroscan Stim2 software; Compumedics). All three sampling rates were presented as randomly interleaved trials within a single presentation block, such that a total of 16,000 trials were presented. The test block consisted of 4000 trials each of the 22 and 96 kHz stimuli and 8000 trials of the 44 kHz stimulus. Doubling the 44 kHz condition allowed for test-retest analysis of neural responses. For each sampling rate condition, half of the trials were presented with inverted polarity.

Experimental Method: Stimulus Analysis. Recordings of each stimulus were made using an A-weighted sound level meter (Bruel & Kjaer, Type 2238 Mediator) recording directly from the ear tube of the transducer (ER2 insert earphone, Etymotic Research) with the same intensity and inter-stimulus interval used in presentation to subjects. The output of the sound level meter was recorded through the line-input of a MacBook Pro (Apple) using LogicPro 9 recording software at a sampling rate of 96 kHz and a bit depth of 24 bits.

Stimulus recordings included 400 repetitions of each sampling rate (22; $44_1$; 96) and a second block of the 44 kHz stimulus ($44_2$). Fast-Fourier transform (FFT) yielded 1600 total corresponding stimulus spectra, each with a frequency resolution of 0.1 Hz. Inter-spectrum correlation analysis was performed between each repetition of each condition for three test comparisons ($22/44_1$; 22/96; $44_1/96$) and a control comparison ($44_1/44_2$). Fisher transform of the resulting r-values yielded normally distributed z'-scores for each individual repetition correlation. Pairwise Bonferroni-corrected t-tests and effect sizes were computed between comparisons.

Experimental Method: Neural Response Measurement. Measurement of the FFR was conducted using a PC-based hardware/software EEG system (Scan 4.3 Acquire, Neuroscan; Compumedics) and four Ag—AgCl scalp electrodes recording differentially from the center vertex of the head (Cz, active) with linked earlobe references and a forehead ground. Contact impedance was ≤5 kΩ for all electrodes and ≤2 kΩ between electrodes. Recording sampling rate was 20 kHz. In order to monitor quality of incoming data, a filtered average (100-2000 Hz) was viewed during response recording using Scan 4.3 (Neuroscan Acquire software; Compumedics). Final averages used in analysis were created offline (Matlab; procedure described below) from a broadband (0.1-3500 Hz) response that was recorded simultaneously. Due to the 1-2 kHz bandwidth limit of auditory midbrain (Liu et al., 2005; White Schwoch et al., 2016), a recording filter of 0.1-3500 Hz and a 20 kHz recording sampling rate are appropriate.

For each subject, a click-evoked auditory brainstem response (ABR) measurement was conducted monaurally in each ear (3000 trials per ear) before and after the test block to 1) verify normal peripheral auditory system function, and 2) ensure reliability over the duration of the test block, especially with respect to proper eartube insertion. Subjects watched a muted movie of their choice with subtitles during testing. All components of the test protocol were performed for every subject.

Experimental Method: Neural Response Data Preparation. Average neural response waveforms were created for each sampling rate condition (22; $44_1$; $44_2$; 96 kHz) for each polarity (A; B) for each subject (n=12). Average waveforms were created for each subject from the first 2000 non-artifact-rejected (>+/−35 uV) responses obtained for each stimulus/polarity condition in a −40 to 245 ms time window, referenced to stimulus onset. Responses of opposing polarities were then added ($A_0B_0$) or subtracted ($A_0B_\pi$) to create two distinct types of response waveforms. Adding the two response polarities ($A_0B_0$) cancels the spectral components of the evoking stimulus, as well as the cochlear microphonic, and emphasizes the natural distortions of the nonlinear central auditory system. Subtracting the two response polarities ($A_0B_\pi$) cancels auditory system distortions and emphasizes the neural analogues of stimulus components, including fundamental frequencies and harmonics (Aiken & Picton, 2008). Importantly, the separation of these two types of responses is not complete, as other components, such as distortion products generated in the cochlea in response to two-tone stimuli, may be present in both $A_0B_0$ and $A_0B_\pi$. Additionally, previous tone-evoked FFR studies have shown some overlap in the presence of stimulus components and distortion products, including response peaks at twice the evoking frequency in the $A_0B_0$ response (Sohmer et al., 1977).

Response waveforms were Hanning-ramped and demeaned. A 200,000-point FFT was performed on the 20-200 ms portion of each response waveform. All subsequent spectral analysis was performed within a 30-2000 Hz bandwidth, chosen to eliminate extraneous low-frequency noise and because most neural response data above 2000 Hz fell below the noise floor. By excluding activity below 30 Hz and above 2000 Hz, we therefore minimize the possibility that differences between responses are due to non-auditory neural activity.

Experimental Method: Neural Response Analysis. Two methods were used to examine a sampling rate effect between the measured neural response spectra; inter-spectrum correlations and discrete peak amplitude and frequency comparisons in the frequency domain. Time-domain waveforms were not used in any analysis.

Experimental Method: Neural Response Correlation Analysis. Inter-spectrum response correlations were performed on an individual subject level for each of four possible comparisons ($44_1/44_2$; $22/44_1$; $44_1/96$; $22/96$). Response spectra obtained in the $44_1$ condition were used for all test correlations involving the 44.1 kHz sample. Neural responses obtained in the $44_2$ condition were used for control analysis only.

Fisher transform of the resulting r-values yielded normally distributed z'-scores for each comparison for each subject to be used in subsequent statistical analysis. Z'-scores were then averaged across subjects to yield a grand average z'-score for each comparison. Repeated-measures ANOVA was performed to determine the effect of sampling rate condition.

Experimental Method: Neural Response Peak Analysis. Individual peaks within the response spectra ($A_0B_0$; $A_0B_\pi$) were analyzed to determine 1) the response frequencies at which significant differences in spectral amplitude occurred, and 2) the relationship of these frequencies to expected response peak frequencies. Expected response frequencies were established for the interval used in the current study (99 and 166 Hz) in a previous study (Lee et al., 2015), which took into account both frequency components of the chord as well as distortions produced by the auditory system. Results for the $A_0B_0$ recordings are shown below in Table 1.

Table 1 includes individual response peak spectral amplitude analysis for the $A_0B_0$ response. A significant main effect of sampling rate occurred at 5 of 22 peaks (shaded rows). Pairwise comparisons revealed that the effect was driven by a difference in spectral amplitude between the 22 kHz response spectra and the other two sampling rates ($22/44_1$ and $22/96$). No significant difference in peak amplitude was observed in the $44_1/96$ or control ($44_1/44_2$) comparisons. A frequency shift, >3 Hz from the nearest expected peak frequency, occurred in the 22 kHz response at 4 of the 5 peaks showing a significant main effect of sampling rate, as well as 2 additional peaks that showed a trending effect, in a majority of subjects (Table 1, column 9).

Expected response frequencies from Lee et al. (2015) included additions and subtractions of the two fundamental frequencies and their harmonics, as well as the common subharmonic and its harmonics in the $A_0B_0$ response (Table 1, column 3).

Peaks of interest were chosen from the spectra obtained in this study following the simple criterion that at least one of the sampling rate conditions (22; $44_1$; 96 kHz) showed a definable peak above the noise floor, which included 10 peaks for $A_0B_\pi$ and 22 peaks for $A_0B_0$ (column 1 of Tables 1 and 2). Importantly, analysis was not limited to peaks identified in Lee et al. (2015), and thus further included analysis of 7 additional peaks for $A_0B_0$. Differences in spectral amplitude were then analyzed using repeated-measure ANOVA.

Results: Stimulus Analysis. Inter-spectrum correlation analysis of 400 repetitions of each stimulus ultimately yielded a final average r-value and z'-score for each comparison ($22/44_1$; $22/96$; $44_1/96$; $44_1/44_2$). Very high correlations were observed for all comparisons, with the highest correlation observed for the control comparison, $44_1/44_2$ (r>0.9999, z'=4.96), and the $44_1/96$ condition (r=0.9999, z'=4.94). A small decrease was noted for the two compari-

TABLE 1

Response Peak Analysis: $A_0B_0$

| Observed Response Peak Frequency (Hz) | Relationship to $f_1$, $f_2$ | Expected Peak Frequency (Hz) | Main Effect of Sampling Rate (p) | $22/44_1$ | $22/96$ | $44_1/96$ | $44_1/44_2$ Control | Peak Frequency Shift for 22 (% of subjects) |
|---|---|---|---|---|---|---|---|---|
| 68 | 2SH, $f_2 - f_1$ | 66, 67 | | | | | | |
| 130.7 | $3f_1 - f_2$ | 131 | | | | | | |
| 132 | 4SH | 132 | | | | | | |
| 138.8 | — | — | $4.6^{-4}$ | *** | *** | | | ✓ (83%) |
| 193 | — | — | 0.06 | * | * | | | ✓ (92%) |
| 196.5 | $2f_1$, 6SH | 198 | | | | | | |
| 199.9 | $2f_1$, 6SH | 198 | | | | | | |
| 207.5 | — | — | 0.06 | * | * | | | ✓ (83%) |
| 331.7 | $2f_2$, 10SH | 330, 332 | | | | | | |
| 397.5 | [$4f_1$, 12SH], $3f_1 - f_2$ | 396, 399 | | | | | | |
| 464.1 | $f_2 + 3f_1$ | 463 | | | | | | |
| 468.4 | — | — | $<1.0^{-8}$ | *** | *** | | | ✓ (92%) |
| 523.7 | — | — | 0.015 | *** | ** | | | ✓ (75%) |
| 528.9 | 16SH, $2f_2 + 2f_1$ | 528, 530 | 0.09 | * | | | | |
| 594.5 | $6f_1$, 18SH | 594 | | | | | | |
| 663.3 | $4f_2$ | 664 | | | | | | |
| 726.5 | 22SH | 726 | | | | | | |
| 795.9 | 24SH | 792 | | | | | | |
| 800.9 | — | — | <0.0001 | *** | *** | | | ✓ (83%) |
| 856.6 | 26SH | 858 | 0.03 | ** | *** | | | |
| 861.4 | 26SH | 858 | | | | | | |
| 996.2 | — | — | | | | | | |

Figure 4:
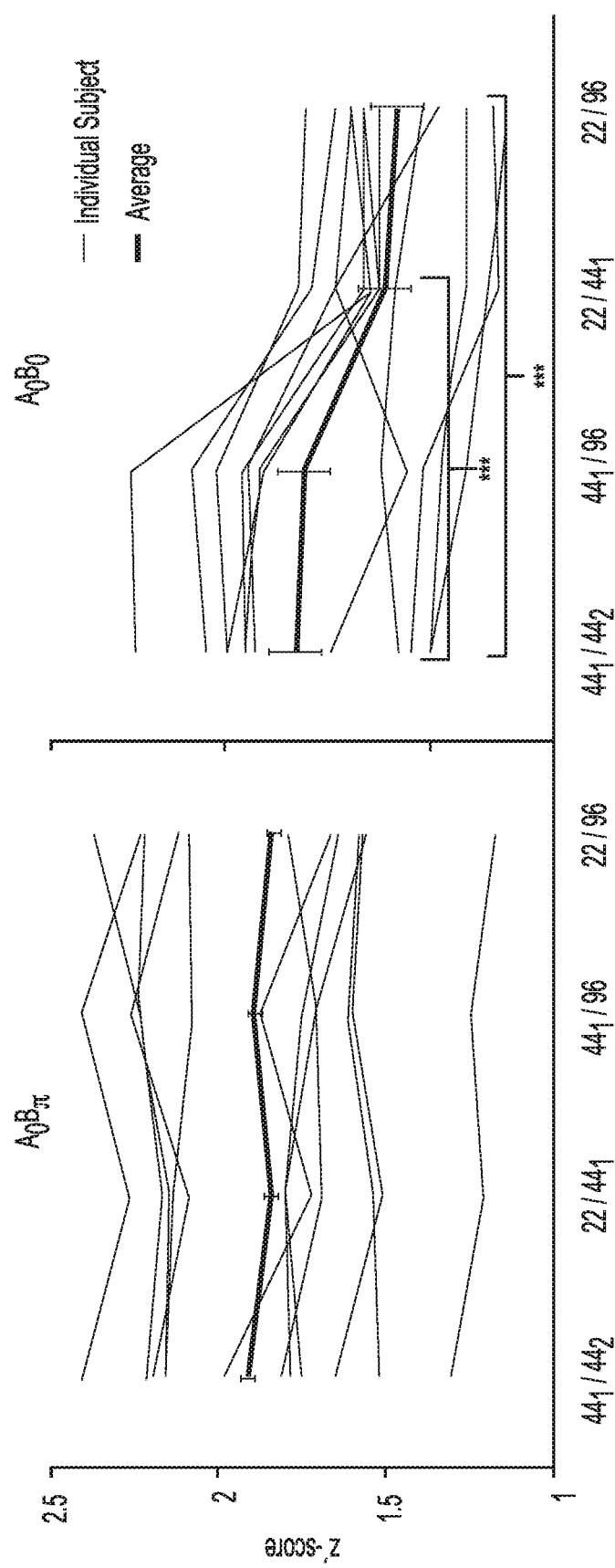
FIG. 4 depicts a graph showing the grand average neural response correlations for each possible sampling rate comparison, for both subtracted ($A_0B_\pi$) and added ($A_0B_0$) responses, as described in the Examples herein. Regarding the subtracted responses ($A_0B_\pi$), no significant difference was observed between any sampling rate comparison, with all showing high correlation. Regarding the added responses ($A_0B_0$), significantly lower correlations were observed for the comparisons involving the 22 kHz response (p=<0.001), relative to the control comparison. The pattern of reduced inter-spectrum correlations between 22 kHz and the two higher sampling rates is observed for ten of twelve subjects (thin lines). There was no significant difference between the control $44_1/44_2$ and $44_1/96$ comparisons (p=0.21).

\* p = <0.05
\*\* p = <0.01
\*\*\* p = <0.001 sons involving the 22 kHz stimulus ($44_1/22$: r=0.9998, z'=4.74; and 96/22: r=0.9998, z'=4.66) (FIG. 2), a pattern also observed in $A_0B_0$ neural response correlations (FIG. 4). Bonferroni-corrected t-tests between the control condition's z' scores and the other z'-scores involving the control (e.g. $44_1/44_2$ vs. $44_1/96$) all were highly significant due to the extremely large number of samples (79,800) involved in this analysis. However, Cohen's effect size calculations confirmed that there was a meaningful difference between the strength of the control-condition inter-stimulus correlations and the two conditions involving the 22 kHz stimulus ($44_1/44_2$ vs. $44_1/22$, d=1.13; $44_1/44_2$ vs. 96/22, d=1.55). In contrast, the 44/96 comparison did not meaningfully differ from the control (d=0.06).

Figure 3:
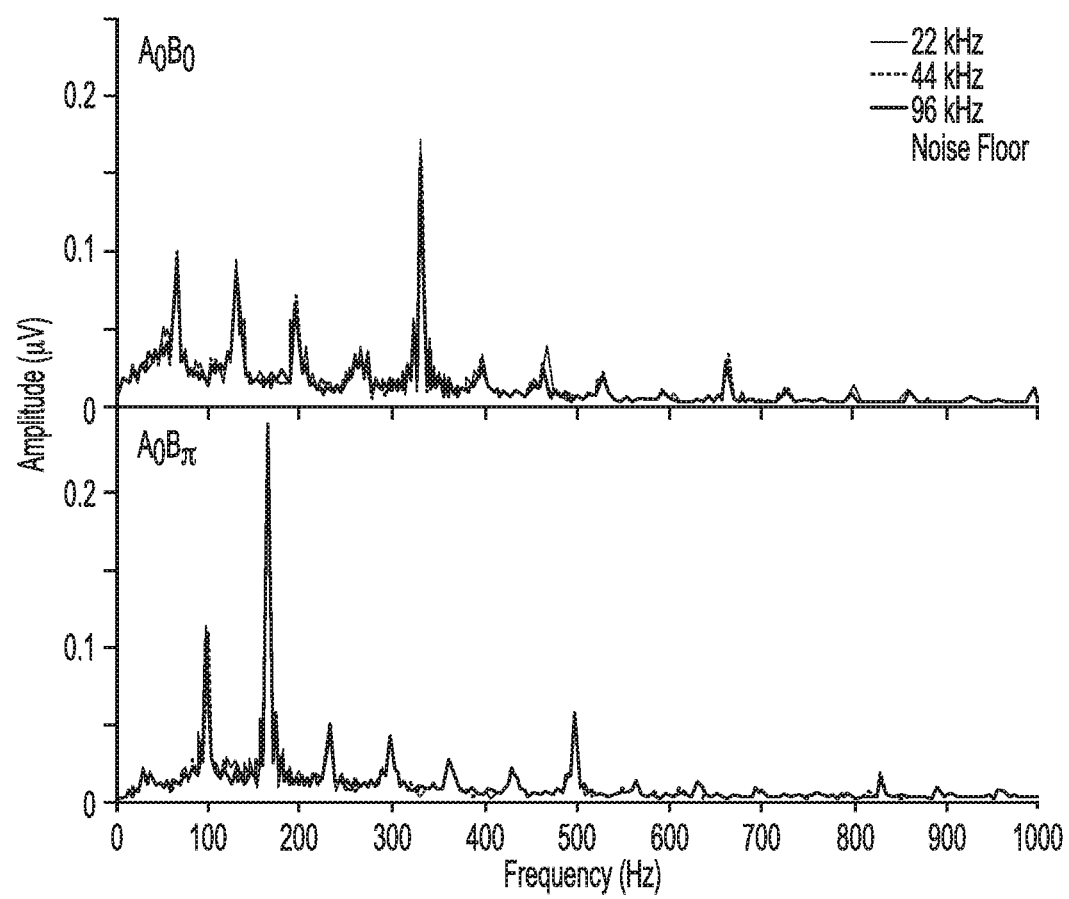
FIG. 3 depicts a graph showing the grand average neural response spectra (n=12) for 22, 44, and 96 kHz conditions, as described in the Examples herein. Neural responses to 4,000 repetitions of each chord, half presented with inverted polarity, were measured for each subject. Adding the two response polarities ($A_0B_0$) emphasized natural distortions of the nonlinear auditory system. Subtracting the two response polarities ($A_0B_\pi$) emphasized the neural analogues of stimulus spectral components, including fundamental frequencies (99 and 166 Hz) and harmonics. Neural response data above the noise floor was minimal for frequencies greater than 1000 Hz.

Results: Neural Response Correlation Analysis. Neural response spectra ($A_0B_\pi$; $A_0B_0$) for the three sampling rate conditions are illustrated in FIG. 3. Correlation analysis of the grand average neural response spectra showed a significant effect of sampling rate for the $A_0B_0$ condition (FIG. 4, right). The control comparison ($44_1/44_2$), as expected, showed a very high correlation of the response spectra, r=0.95 (z=1.77). Likewise, the spectrum correlation between the two higher sampling rates ($44_1/96$) was also high (r=0.94, z'=1.74) and not significantly lower than the control condition (p=0.21). In contrast, the spectrum correlations that involved the 22 kHz condition, though still strong, were significantly lower than the control ($44_1/22$: r=0.91, z'=1.50, p<0.001 and 96/22: r=0.91, z'=1.46, p<0.001). The pattern of reduced inter-spectrum correlations between 22 kHz and the two higher sampling rates is observed for ten of twelve subjects (FIG. 4, thin lines). Pair wise comparisons were made using Bonferroni-corrected t-tests.

For the $A_0B_\pi$ condition, there were no significant differences among any of the response spectra, with all pairs showing high correlations (r=0.95–0.96; z'=1.8–1.9) (FIG. 4, left).

Figures 5A, 5B:
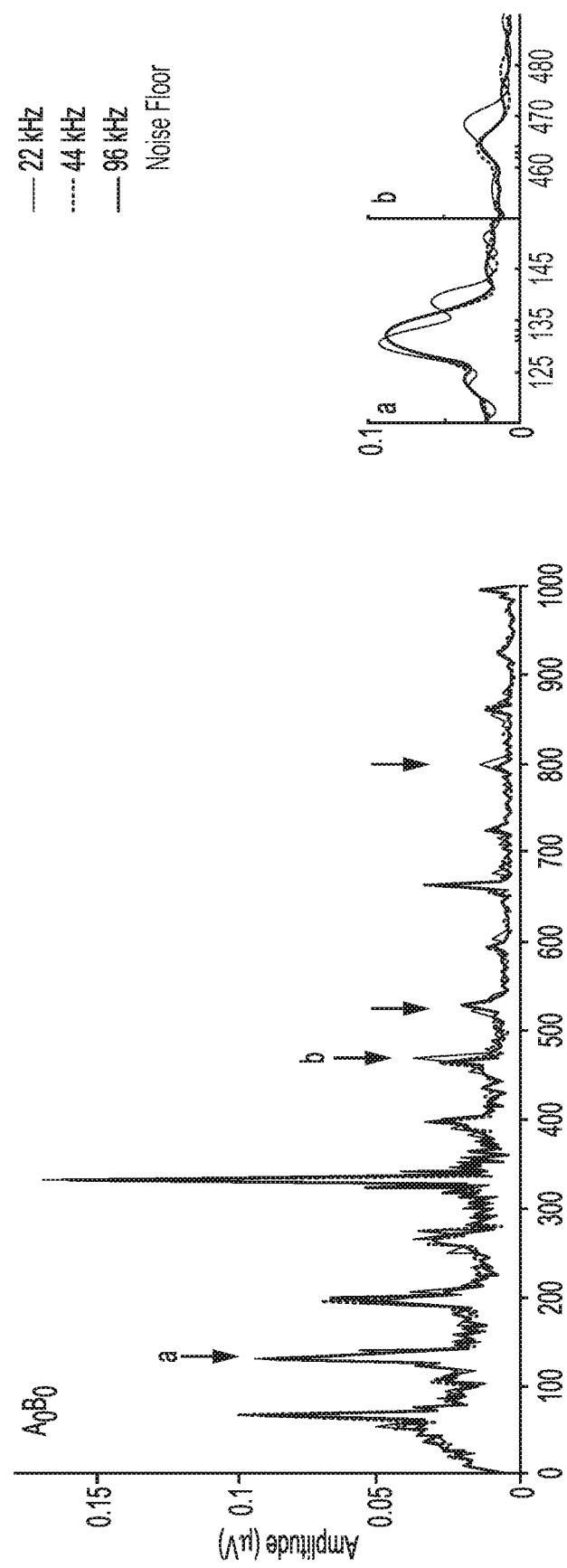
FIG. 5A (main graph) depicts a graph showing the grand average neural response spectra ($A_0B_0$), as described in the Examples herein. Arrows indicate regions of significant difference in spectral amplitude between sampling rate conditions. These regions showed a frequency shift (>3 Hz) in 22 kHz response peaks, which, in turn, created significant differences in spectral amplitude for 22 kHz relative to 44 and 96 kHz conditions. In order of ascending frequency (Hz), peaks showing both significant difference in 22 kHz amplitude as well as a frequency shift include: 138.8 Hz (expected=132, 4SH), 468.4 (expected=463, f2+3f1), 523.7 (expected=528, 16SH), 800.9 (not expected).
FIG. 5B (inset) is a graph depicting examples of the observed frequency shift of FIG. 5A. The shaded boxes mark the expected frequencies, +/−1 Hz. A shift was clearly observed at two additional peaks that did not meet significance criteria in spectral amplitude analysis.

Results: Neural Response Individual Peak Analysis, $A_0B_0$. Analysis of individual response peaks revealed a significant main effect of sampling rate on spectral amplitude at 5 of 22 peaks, with another three trending. Pairwise comparisons revealed that the main effect was driven by a difference in spectral amplitude for the 22 kHz response relative to the 44 and 96 kHz responses (Table 1). It was discovered that at 4 of these 5 peaks, a peak frequency shift (>3 Hz from nearest expected) had occurred only in the 22 kHz response which, as a result, created the significant difference in spectral amplitude at the expected frequency (FIG. 5). A frequency shift (>3 Hz) was observed at 3 additional peaks that showed only trending significance in spectral amplitude difference. Moreover, the frequency shifts were observed for the majority of subjects (Table 1, column 9).

In the control and 44/96 kHz response comparisons, no significant difference in spectral amplitude or apparent frequency shift was observed at any response peak (Table 1, columns 6 and 7).

Results: Neural Response Individual Peak Analysis, $A_0B_\pi$. No main effect of sampling rate was observed at any response peak (see Table 2 below).

TABLE 2

Response Peak Analysis: $A_0B_\pi$

| Response Peak Frequency (Hz) | Relationship to $f_1, f_2$ | Expected Peak Frequency (Hz) | Main Effect of Sampling Rate | $44_1/44_2$ (Control) | $22/44_1$ | $44_1/96$ | $22/96$ | Peak Frequency Shift for 22 |
|---|---|---|---|---|---|---|---|---|
| 30.2 | $2f_1 - f_2$, SH | 32, 33 | | | | | | |
| 99 | $f_1$ | 99 | | | | | | |
| 165.7 | $f_2$ | 166 | | | | | | |
| 233.2 | $2f_2 - f_1$ | 233 | | | | | | |
| 297 | $3f_1$, 9SH | 297 | | | | | | |
| 361 | 11SH, $2f_1 + f_2$ | 363, 364 | | | | | | |
| 429 | 13SH, $f_1 + 2f_2$ | 430, 431 | | | | | | |
| 497.7 | $3f_2$ | 498 | | | | | | |
| 563 | $4f_2 + f_2$ | 562 | | | | | | |
| 830 | $5f_2$ | 830 | | | | | | |

* p = <0.05
** p = <0.01
*** p = <0.001

Table 2 presents individual response peak spectral amplitude analysis for the $A_0B_\pi$ response. No main effect of sampling rate was observed at any response peak frequencies. No shift in peak frequency >3 Hz was observed at any peak.

Discussion: Through investigation with the frequency following response (FFR), it was determined that the auditory brain distinguishes stimuli encoded with different sampling rates. Spectral analysis of neural responses revealed that the lowest sampling rate condition, 22 kHz, differed significantly from 44 and 96 kHz conditions, which themselves did not differ from one another relative to a control comparison. The results suggest an effect of decreasing sampling rate as well as the existence of a neural discrimination ceiling above which differences are not observed. Ultimately, the results show that the auditory brain is capable of distinguishing stimuli that differ only in the sampling rate with which they were encoded.

Sampling rate effects on the stimuli were also considered. The similar correlational trends observed for stimuli and neural responses suggest that differences observed in the 22 kHz response spectra were in fact elicited by acoustic differences in the 22 kHz stimulus (FIG. 2 and FIG. 4).

The sampling rate effect on the test stimuli was subtle. Sampling rate alone did not produce dramatic changes in stimulus amplitude or frequency content with the use of a low-frequency-biased triangle wave stimulus. This was proven true in the results, as the correlational effect in the stimuli was present but small, such that determination of the exact differences in frequency content that were driving a decrease in 22 kHz correlations were difficult to realize in a meaningful way. Close inspection of the three spectra overlaid revealed that any observable spectral differences for 22 kHz were slight, were not more prevalent in any specific frequency region, showed no apparent pattern of increased or decreased spectral amplitude, and appeared no greater than those observed between 44 and 96 kHz. Importantly, the conspicuous peak frequency shifts observed in $A_0B_0$ 22 kHz neural response were not present in the 22 kHz stimulus.

Despite unknowns in determining the exact mechanism underlying the 22 kHz stimulus difference, inter-spectrum correlation analysis of numerous individual repetitions yielded consistently lower correlations in all comparisons that included the 22 kHz stimulus, supported by effect size calculations that identified a meaningful difference between comparisons. Considering neural response results, the stimulus analysis results suggest the existence of a small stimulus sampling rate effect that was nonetheless large enough to produce a significant effect in the auditory brain's processing of the stimuli.

Sampling rate effects on neural responses were evaluated. The ability of the auditory brain to distinguish sampling rate was shown through spectral correlation analysis of the neural responses elicited by the three test stimuli. The results indicate that the neural response elicited by the 22 kHz stimulus differed significantly from those elicited by the 44 and 96 kHz stimuli, which in turn did not differ from each other. The subtle nature of the differences in the 22 kHz stimulus, as previously discussed, may underlie the unexpected result that a neural response sampling rate effect was observed only in the added, $A_0B_0$, response condition.

Auditory System Nonlinearities and the $A_0B_0$ Response. A sampling rate effect was observed only in the neural response condition in which the two polarities were added ($A_0B_0$), a process that effectively cancels the spectral components of the evoking stimulus from the neural response. This method has been used to emphasize phase locking to the envelope of the stimulus and minimize the cochlear microphonic (Skoe & Kraus, 2010). For the current discussion, the most critical consequence of adding response polarities is the emphasis of natural distortions generated by nonlinearities of the auditory system (Aiken & Picton, 2008).

The neural response to a complex stimulus, such as the musical interval used in this study, is not simply an analogue of stimulus characteristics. The acoustic interactions of the interval components ($f_0$ and harmonics) are processed in a nonlinear manner by the auditory system, generating neural frequencies that do not exist acoustically but appear in the spectra of the FFR. The generation of these additional frequency components, or distortion products (DPs), is complex, arising as a result of first and possibly second-order frequency interactions along the auditory pathway. DPs can be generated at the level of the cochlea by nonlinearities in outer hair cell motion (Robles et al., 1991) or more centrally, as in the generation of envelope-related DPs and a common subharmonic in response to consonant intervals (Lee et al., 2015).

With this consideration, it was an unexpected and fascinating finding that a sampling rate effect was observed only in the response condition that emphasized auditory system DPs ($A_0B_0$), and not in the response condition that emphasized spectral components of the stimulus ($A_0B_\pi$). With the use of far-field potential recordings, we cannot determine whether the DPs observed in the $A_0B_0$ response reflect peripheral or central nonlinearities. However, the results suggest that differences in DP frequencies are driving the observed sampling rate effect.

Summarily, the results suggest that decreasing sampling rate has an effect not on the mirror neural representation of a stimulus, but on the way in which nonlinearities of the auditory brain contribute to the evoked response.

Individual Response Peak Analysis: The 22 kHz Frequency Shift. Spectral amplitude analysis of individual response peaks led to an unexpected discovery of shifts in the peak frequencies of the 22 kHz $A_0B_0$ response. A shift of greater than 3 Hz away from the mathematically expected peak was observed at a total of 7 peaks, 4 of which also showed a significant difference in spectral amplitude (with the remaining 2 trending). Only one expected peak (858 Hz) showed a significant difference in spectral amplitude without a frequency shift.

The influence of outliers was ruled out, as nearly identical shifts (degree and direction) were observed at the level of individual subjects for each peak (Table 1, column 9). However, between the peaks exhibiting a shift, there was no discernable pattern in the direction or degree of the shift: in some instances the shift was toward a lower frequency, in others a higher frequency. In fact, several peaks exhibited a "multi-peaked" pattern in the 22 kHz response in regions where well-defined single peaks were present for 44 and 96 kHz conditions (FIG. 5, inset a).

A Sampling Rate Effect Within a Limited Bandwidth. Increasing or decreasing sampling rate affects the upper limit of the bandwidth that can be accurately encoded and subsequently reproduced, termed the Nyquist frequency (NF). With higher sampling rates, the Nyquist frequency increases and higher frequencies can be faithfully encoded. Interestingly, it is theoretically accepted that increasing sampling rate has no effect on lower frequency components, despite an increase in sample points for those frequencies. In a relevant example, it would be predicted that the increase in sampling rate from 22.05 kHz (NF: 11.025 kHz) to 44.1 kHz (NF: 22.05 kHz) would have no acoustic effect on the signal below 11.025 kHz.

Decades of intense and largely unresolved debate in the recording community, as well as the discrimination findings of Pras and Guastavino (2010), support the need for more controlled investigation of how sampling rate influences lower spectral components. Anecdotal claims of the ability to distinguish between 44.1 kHz and higher sampling rates were supported by the controlled findings of Pras and Guastavino (2010). However, all listeners were limited by the same accepted bandwidth of human sensitivity, 20-20,000 Hz, well below any additional frequency information introduced with an increase from a 44.1 kHz sampling rate. Although the ultrasonic effect discovered by Oohashi et al. (2000) may have produced physiological changes in the subjects of Pras & Guastavino (2010), it is unlikely that it allowed for the observed discrimination ability, as subjects in Oohashi et al. (2000) did not perceive the presentation of ultrasonic frequencies.

These considerations led to a primary goal of this study; the determination of a sampling rate effect within a lower, limited bandwidth. This design allowed for the additional benefit of ecological validity. Bandwidth limitations are ubiquitous in the world of digital audio, including those imposed by common audio reproduction devices (e.g. headphones, speakers), assistive devices (e.g. hearing aids), and ultimately the limits of biological sensitivity (20-20,000 Hz).

The results discussed herein showed a measurable neural effect of decreasing sampling rate from 44 to 22 kHz within a bandwidth limited by the use of low-frequency biased triangle-wave stimuli, with little to no acoustic content above the lowest Nyquist frequency, 11.025 kHz, in any of the stimuli. In fact, little to no acoustic content was present in any stimulus beyond ~7000 Hz. The FFR is even further bandwidth-limited in that responses above ~2000 Hz are rarely measurable. The discovery that the effect was driven by frequency shifts in auditory system DPs hints at a more subtle and complex mechanism underlying the effect of essentially lower-fidelity AD conversion on listener physiology. If it was desired to limit any frequency distortion effects in order to maximize the experience of a listener, the results would support the use of a sampling rate higher than the minimum proposed by the Nyquist-Shannon theorem for a given bandwidth.

Current Technologies: Hearing Aids. The effect of decreasing sampling rate to 22 kHz is less applicable to most modern recording and reproduction devices, as low-cost hardware interfaces and free recording software are now capable of sampling rates often exceeding 44.1 kHz. The 22 kHz effect is more appropriately discussed in relation to technologies that are still limited to lower sampling rates, perhaps most importantly, hearing aids and other assistive listening devices.

The stage has been set for hearing aids to become more accessible and affordable in the near future than ever before. At the national level, priorities for hearing healthcare were set forth by the National Academies of Sciences, Engineering, and Medicine in a landmark publication focused on improving accessibility and affordability (NASEM, 2016), followed within a year by the introduction of the Over-the-Counter Hearing Aid Act of 2017. In private industry, new players are entering the hearing aid market, from start-up developers of personal sound amplification products (PSAPs) to technological giants. A centerpiece of much discussion has been the technological specifications that will be required of hearing aid manufacturers as accessibility improves.

Improvements in digital hearing aid technology have included reduced size, increased battery life, inclusion of a telecoil, feedback reduction, and wireless connectivity (NASEM, 2016). Signal processing has also improved, including development of new compression algorithms and automatic noise reduction features based on real-time input analysis.

However, reproducible bandwidth has not shown a remarkable increase. Despite research showing a degradation in perceived sound quality when upper cutoffs were reduced for speech (below 10,869 Hz) and music (below 16,854 Hz) (Moore & Tan, 2003), hearing aids rarely amplify sound above 8,000 Hz, and there has been only recent development of devices that claim to reproduce up to 10,000 Hz. Transducer limitations are often given as the cause of this bandwidth limit, but this obstacle seems increasingly unlikely given the rapid development of small, high-fidelity devices in other markets, and contradicts reports of hearing aids with the capability of reproducing up to 16 kHz as long ago as the 1980's (Killion, 2009). It may also be considered that a traditional audiological assessment (125-8000 Hz) is used almost exclusively for programming and verification of appropriate amplification. Due to the current limits of hearing aid bandwidth and the influence of the Nyquist-Shannon theorem, hearing aid manufacturers have not been obligated to increase sampling rate, as 16 kHz is theoretically sufficient to encode information up to 8000 Hz.

A Neural Discrimination Ceiling. Perhaps just as meaningful as an effect of decreasing sampling rate, albeit for a different population of listeners, is the null finding for the 44/96 kHz comparison. In conjunction with the observed 22 kHz effect, this null finding suggests the existence of a neural discrimination ceiling at a sampling rate frequency between 22.05 and 44.1 kHz, above which the auditory brain does not distinguish sampling rate.

The null result is a neural contradiction to the behavioral findings of Pras & Guastavino (2010), who showed that trained ears were able to discriminate 44.1 and 88.2 kHz in an AB comparison task.

The results discussed herein show that decreasing sampling rate has a significant effect on the neural representation of a musical interval, an effect driven by frequency shifts in the frequency following response of the auditory brain to the lowest sampling rate condition, 22.05 kHz. This finding suggests that hearing aid users may especially benefit from the use of devices with sampling rates higher than current industry standards. Additionally, this study is the first to objectively show that the auditory brain does not benefit from an increase in sampling rate above a current music-industry standard, 44.1 kHz.

Systems

Figure 6:
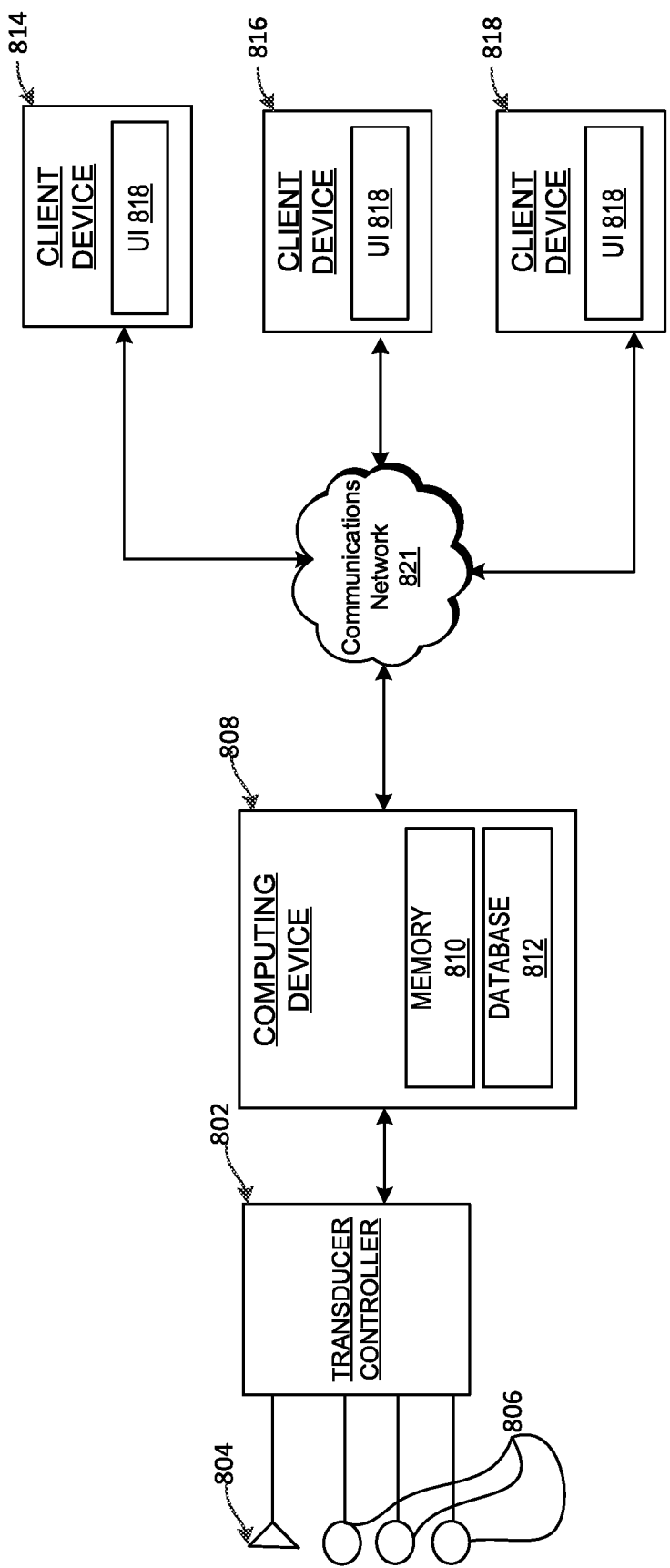
FIG. 6 is an example computing environment, according to aspects of the present disclosure.

FIG. 6 illustrates a computing environment and/or computing system 800 that automatically transmits acoustic stimuli, receives and processes brain response data, and automatically determining how the brain distinguishes between variations of a digital sound, thereby indicating whether and to what extent digital processing impacts how the human brain processes sounds. More specifically, FIG. 6 illustrates a computing environment and/or computing system 800 including a server computing device 808 operating in conjunction with various other hardware and/or software components that may be used to perform or otherwise execute the various processes described herein.

Referring initially to FIG. 6, the computing environment 800 includes a transducer controller 802 functionally coupled to an acoustic transducer 804 and one or more electrodes 806. More specifically, the transducer controller 802 represents a computing and/or processing device that delivers a stimulus to the acoustic transducer 804. Additionally, the transducer controller 802 may receive and process brainwave signal information from the one or more electrodes 806. The transducer controller 802 may be any suitable stimulus delivery and data acquisition system, including PC-based stimulus delivery and data acquisition systems such as those available from Bio-logic Systems Corporation or Compumedics. The acoustic transducer 804 may be an insert earphone such as the ER-3 insert earphone available from Etymotic Research, Elk Grove, Ill. The one or more electrodes 806 may be Ag—AgCl scalp electrodes, which may be positioned on the test subject from Cz (active) to ipsilateral earlobe (reference) with forehead ground.

The transducer controller 802 may be functionally connected to a computing device 808 including a memory 810 within which instructions are retained directing the operation of the computing device 808 for carrying out the herein described methods and processes. More specifically, the computing device 808 automatically generates a test stimulus signal, communicates the test stimulus signal to the transducer controller 802 for generation of an acoustic stimulus that is presented or otherwise provided to the test subject via the acoustic transducer 804. The computing device 808 may obtain brain response data via the electrodes 806 and the transducer controller 802. The brain response data may be stored within the memory 810 and/or stored or otherwise maintained in a database 812.

The computing device 808 may transmit the brain response data to one or more client devices 814-820. The one or more client devices 814-820 functionally communicate with the computing device 808 through a communications network 821, which may be the Internet, an intranet, an Ethernet network, a wireline network, a wireless network, and/or another communication network. The one or more client devices 814-820 may be a personal computer, work station, mobile device, mobile phone, tablet device, processor, and/or other processing device capable of implementing and/or executing processes, software, applications, etc., that includes network-enabled devices and/or software, such as user-interface 818 for communication over the communications network 112 (e.g., browsing the internet). Additionally, the one or more client device(s) 814-820 may include one or more processors that process software or other machine-readable instructions and may include a memory to store the software or other machine-readable instructions and data.

The database 812 may include one or more data structures used to stored data for analysis of the acquired brain response data. For example, the database 812 may contain one or more data structures containing normative response data to which the acquired brain response data may be compared to provide comparison data. The database 812 may further contain criteria data for evaluating the comparison data for determining the existence of a non-penetrating brain injury.

Figure 7:
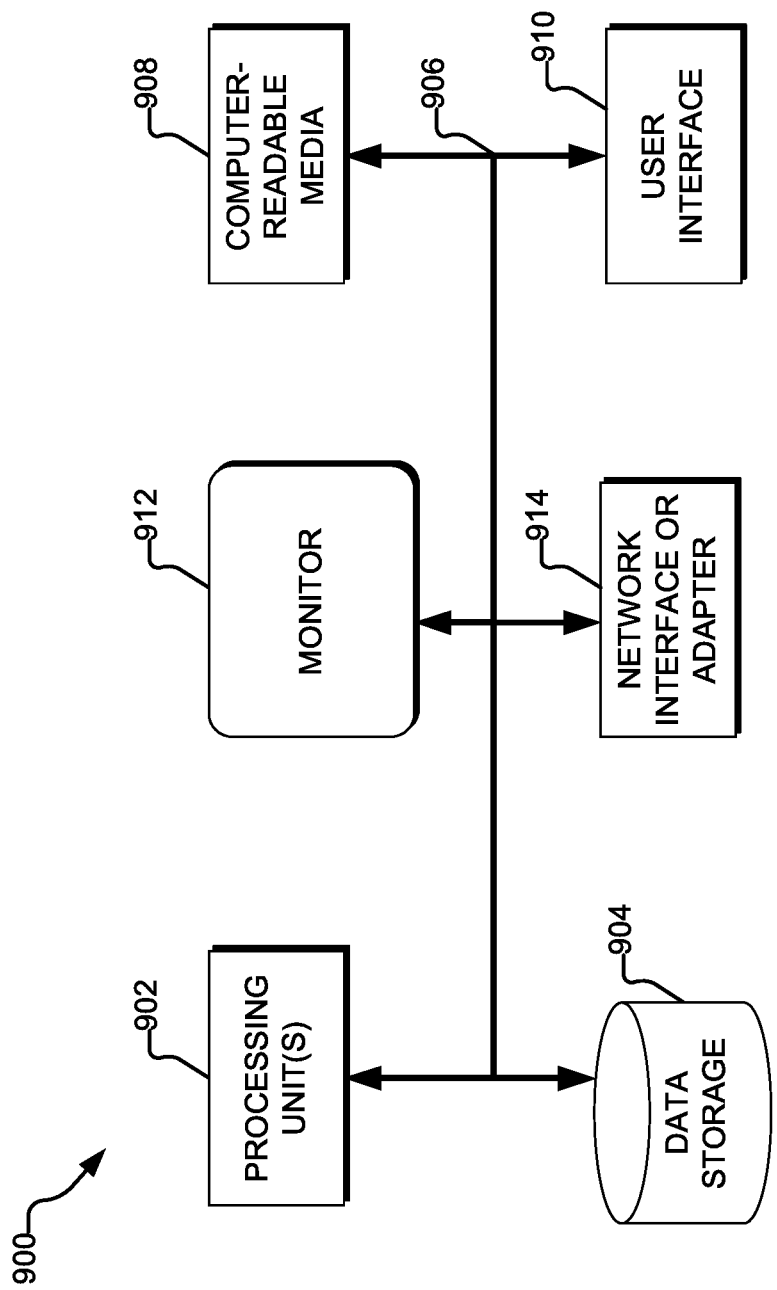
FIG. 7 is an example computing system or device, according to aspects of the present disclosure.

FIG. 7 illustrates an example of a suitable computing and networking environment 900 that may be used to implement various aspects of the present disclosure. As illustrated, the computing and networking environment 900 includes a general purpose computing device 900, although it is contemplated that the networking environment 900 may include other computing systems, such as personal computers, server computers, hand-held or laptop devices, tablet devices, multiprocessor systems, microprocessor-based systems, set top boxes, programmable consumer electronic devices, network PCs, minicomputers, mainframe computers, digital signal processors, state machines, logic circuitries, distributed computing environments that include any of the above computing systems or devices, and the like.

Components of the computer 900 may include various hardware components, such as a processing unit 902, a data storage 904 (e.g., a system memory), and a system bus 906 that couples various system components of the computer 900 to the processing unit 902. The system bus 906 may be any of several types of bus structures including a memory bus or memory controller, a peripheral bus, and a local bus using any of a variety of bus architectures. For example, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The computer 900 may further include a variety of computer-readable media 908 that includes removable/non-removable media and volatile/nonvolatile media, but excludes transitory propagated signals. Computer-readable media 908 may also include computer storage media and communication media. Computer storage media includes removable/non-removable media and volatile/nonvolatile media implemented in any method or technology for storage of information, such as computer-readable instructions, data structures, program modules or other data, such as RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information/data and which may be accessed by the computer 900. Communication media includes computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. For example, communication media may include wired media such as a wired network or direct-wired connection and wireless media such as acoustic, RF, infrared, and/or other wireless media, or some combination thereof. Computer-readable media may be embodied as a computer program product, such as software stored on computer storage media.

The data storage or system memory 904 includes computer storage media in the form of volatile/nonvolatile memory such as read only memory (ROM) and random access memory (RAM). A basic input/output system (BIOS), containing the basic routines that help to transfer information between elements within the computer 900 (e.g., during start-up) is typically stored in ROM. RAM typically contains data and/or program modules that are immediately accessible to and/or presently being operated on by processing unit 902. For example, in one embodiment, data storage 904 holds an operating system, application programs, and other program modules and program data.

Data storage 904 may also include other removable/non-removable, volatile/nonvolatile computer storage media. For example, data storage 904 may be: a hard disk drive that reads from or writes to non-removable, nonvolatile magnetic media; a magnetic disk drive that reads from or writes to a removable, nonvolatile magnetic disk; and/or an optical disk drive that reads from or writes to a removable, nonvolatile optical disk such as a CD-ROM or other optical media. Other removable/non-removable, volatile/nonvolatile computer storage media may include magnetic tape cassettes, flash memory cards, digital versatile disks, digital video tape, solid state RAM, solid state ROM, and the like. The drives and their associated computer storage media, described above and illustrated in FIG. 7, provide storage of computer-readable instructions, data structures, program modules and other data for the computer 900.

A user may enter commands and information through a user interface 910 or other input devices such as a tablet, electronic digitizer, a microphone, keyboard, and/or pointing device, commonly referred to as mouse, trackball or touch pad. Other input devices may include a joystick, game pad, satellite dish, scanner, or the like. Additionally, voice inputs, gesture inputs (e.g., via hands or fingers), or other natural user interfaces may also be used with the appropriate input devices, such as a microphone, camera, tablet, touch pad, glove, or other sensor. These and other input devices are often connected to the processing unit 902 through a user interface 910 that is coupled to the system bus 906, but may be connected by other interface and bus structures, such as a parallel port, game port or a universal serial bus (USB). A monitor 912 or other type of display device is also connected to the system bus 906 via an interface, such as a video interface. The monitor 912 may also be integrated with a touch-screen panel or the like.

The computer 900 may operate in a networked or cloud-computing environment using logical connections of a network interface or adapter 914 to one or more remote devices, such as a remote computer. The remote computer may be a personal computer, a server, a router, a network PC, a peer device or other common network node, and typically includes many or all of the elements described above relative to the computer 900. The logical connections depicted in FIG. 7 include one or more local area networks (LAN) and one or more wide area networks (WAN), but may also include other networks. Such networking environments are commonplace in offices, enterprise-wide computer networks, intranets and the Internet.

When used in a networked or cloud-computing environment, the computer 900 may be connected to a public and/or private network through the network interface or adapter 914. In such embodiments, a modem or other means for establishing communications over the network is connected to the system bus 906 via the network interface or adapter 914 or other appropriate mechanism. A wireless networking component including an interface and antenna may be coupled through a suitable device such as an access point or peer computer to a network. In a networked environment, program modules depicted relative to the computer 900, or portions thereof, may be stored in the remote memory storage device.

As explained in the various examples above, each step in the analog-to-digital conversion pathway warrants systematic investigation, as each can have an effect on the experience of a listener. For example, decreasing sampling rate has a significant effect on the neural representation of a musical interval, an effect driven by frequency shifts in the frequency following response of the auditory brain to the lowest sampling rate condition, 22.05 kHz. Such a finding suggests that hearing aid users may benefit from the use of devices with sampling rates higher than current industry standards. Additionally, the above-study is the first to objectively show that the auditory brain does not benefit from an increase in sampling rate above a current music-industry standard, 44.1 kHz.

Allen, J., Kraus, N., & Bradlow, A. (2000). Neural representation of consciously imperceptible speech sound differences. Perception and Psychophysics, 62(7), 1383-1393.

Anderson, S., & Kraus, N. (2013). The potential role of the cABR in assessment and management of hearing impairment. Int J Otolaryngol, 2013, 604729.

Appendix 1 is incorporated in its entirety herein.

Chandrasekaran, B., & Kraus, N. (2010). The scalp-recorded brainstem response to speech: origins and plasticity. Psychophysiology, 47 (2010), 236-246.

Gorga, M., Abbas, P., & Worthington, D. (1985) Stimulus calibration in ABR measurements. In J. Jacobson (Ed.), The auditory brainstem response (pp. 49-62). SanDiego, Calif.: College-Hill Press.

He, S., Grose, J. H., & Buchman, C. A. (2012). Auditory Discrimination: The Relationship Between Psychophysical and Electrophysiological Measures. International Journal of Audiology, 51(10), 771-82.

Killion, M. (2009). What Special Hearing Aid Properties Do Performing Musicians Require? The Hearing Review, February, 2009, 20-31.

Kim, J. (2015) Acoustic Change Complex: Clinical Implications. Journal of Otology and Audiology, 19(3), 120-124.

Kraus, N. (2011). Listening in on the listening brain. Physics Today, 64(6), 40-45.

Kraus, N. & White-Schwoch, T. (2015). Unraveling the biology of auditory learning: A cognitive-sensorimotor-reward framework. Trends in Cognitive Sciences, 19(11), 642-654.

Liu, L., Palmer, A. R., & Wallace, M. N. (2005). Phase-locked responses to pure tones in the inferior colliculus. Journal of Neurophysiology, 95(3), 1926-1935.

Lee, K. M., Skoe, E., Kraus, N., & Ashley, R. (2015). Neural transformation of dissonant intervals in the auditory brainstem. Music Perception, 32(5), 445-459.

Martin, G. K., Probst, R., & Lonsbury-Martin, B. L. (1990). Otoacoustic emissions in human ears: Normative findings. Ear and Hearing, 11, 106-120.

MATLAB and Statistics Toolbox Release R2013a [computer software]. Natick, Mass.: The MathWorks, Inc.

Meyer, B., & Moran, D. (2007). Audibility of a CD-Standard A/DA/A Loop Inserted into High-Resolution Audio Playback. Journal of the Audio Engineering Society, 55(9), 775-779.

Moore, B. C. J., & Tan, C.-T. (2003). Perceived naturalness of spectrally distorted speech and music. The Journal of the Acoustical Society of America, 114(1), 408.

National Academies of Sciences, Engineering, and Medicine. (2016). Hearing healthcare for adults: Priorities for improving access and affordability. Washington, D.C.: The National Academic Press.

Nyquist, H. (2002). Certain Topics in Telegraph Transmission Theory. Proceedings of the IEEE, 90(2). (Reprinted from Transactions of the A. I. E. E., pp. 617-644, February 1928).

Pras, A., & Guastavino, C. (2010). Sampling rate discrimination: 44.1 kHz vs. 88.2 kHz. Paper presented at the 128th Audio Engineering Society Convention, London, 22-25 May.

Pras, A., Zimmerman, R., Livitin, D., & Guastavino, C. (2009). Subjective Evaluation of MP3 Compression for Difference Musical Genres. Paper presented at the 127th Audio Engineering Society Convention, New York, 9-12 October.

Robles, L., Ruggero, M. A., & Rich, N. C. (1991). Two-tone distortion in the basilar membrane of the cochlea. Nature, 349, 413-414.

Rosen, S., & Howell, P. (2013). Signals and systems for speech and hearing (Second ed.). Leiden: Brill.

Schweitzer, C. (1997). Development of Digital Hearing Aids. Trends in Amplification, 2(2), 41-77.

Shannon, C. E. (1949). Communication in the presence of noise. Proceedings of the IRE, 37(1), 10-21.

Skoe, E., & Kraus, N. (2010). Auditory brain stem response to complex sounds: A tutorial. Ear and Hearing, 31, 302-324.

Oohashi, T., Nishina, E., Honda, M., Yonekura Y., Fuwamoto, Y., Kawai N. Shibasaki, H. (2000). Inaudible high-frequency sounds affect brain activity: Hypersonic effect. Journal of Neurophysiology, 83(6), 3548-3558.

White-Schwoch, T., Nicol, T., Warrier, C. M., Abrams, D. A., & Kraus, N. (2016). Individual Differences in Human Auditory Processing: Insights From Single-Trial Auditory Midbrain Activity in an Animal Model. Cereb Cortex, 2016, 1-21.

Wiley, T. L., Cruickshanks, K. J., Nondahl, D. M., Tweed, T. S., Klein, R., & Klein, B.

E. (1996). Tympanometric measures in older adults. Journal of the American Academy of Audiology, 7, 260-268.

We claim:

1. A method for developing an audio device, the method comprising:
(a) presenting at least two auditory stimuli to a subject, wherein each auditory stimulus is created by a process that uses different variations of the same digital signal processing technique;
(b) measuring the frequency following response (FFR) elicited by each stimulus and comparing the measurements to identify any positive or negative effects in the FFR elicited by any one of the stimuli; and (c) developing an audio device that converts an analog auditory signal into a digital auditory signal using the digital processing technique determined in step (b) to have a more positive effect or less negative effect on FFR.

2. An audio device produced by the method of claim 1.

3. The method of claim 1, wherein the audio device is an assistive listening device, a speaker, an earphone, or headphones.

4. The method of claim 3, wherein the assistive listening device includes a hearing aid or cochlear implant.

5. The method of claim 1, wherein the digital signal processing technique is a filter, a noise cancellation algorithm, a noise reduction algorithm, a pitch-altering algorithm, a compression algorithm, a distortion, an amplification, or a variation in sampling rate, bit depth, or bit rate.

6. The method of claim 1, wherein measuring the FFR comprises measuring harmonics and/or distortion products generated by the auditory system that are not present in the stimuli.

7. The method of claim 6, wherein measurements of harmonics and/or distortion products present in the FFR but not present in the stimuli are compared to identify any positive or negative effects in the FFR elicited by any one of the stimuli.

8. The method of claim 1, wherein the at least two auditory stimuli are generated from the same source.

9. A method for evaluating the sound quality of a digital engineering process, comprising:

(a) presenting a first auditory stimulus to a subject, wherein the first auditory stimulus is created by a digital engineering process that uses a first digital signal processing technique;

(b) presenting a second auditory stimulus to a subject, wherein the second auditory stimulus is created by the digital engineering process of step (a) but using a variation of the first digital signal processing technique;

(c) measuring the frequency following response (FFR) elicited by each of the first and second auditory stimuli, and comparing the measurements to determine the effect of each stimulus on FFR; and (d) identifying the digital engineering process of step (a) or step (b) resulting in the more positive effect or less negative effect on FFR as the process that provides superior sound quality.

10. The method of claim 9, wherein the digital signal processing technique is a filter, a noise cancellation algorithm, a noise reduction algorithm, a pitch-altering algorithm, a compression algorithm, a distortion, an amplification, a variation in sampling rate, bit depth, or bit rate.

11. The method of claim 10, wherein the digital signal processing technique is a sampling rate.

12. The method of claim 11, wherein the sampling rate is in the range of 22 kHz to about 44 kHz.

13. The method of claim 9, wherein the variation of the first digital signal processing technique is the absence of the first digital signal processing technique.

14. The method of claim 9, wherein the first and second auditory stimuli are generated from the same source.

15. A system for evaluating the sound quality of a digital engineering process, the system comprising a computing device comprising at least one processor configured to perform a method according to claim 8.

16. The system of claim 15, wherein the digital signal processing technique is a filter, a noise cancellation algorithm, a noise reduction algorithm, a pitch-altering algorithm, a compression algorithm, a distortion, an amplification, a sampling rate, a bit depth, or a bit rate.

17. The system of claim 15, wherein the at least one processor is further configured to measure harmonics and/or distortion products generated by the auditory system that are not present in the stimuli.

* * * * *